United States Patent [19]

Beier

[11] 4,446,456

[45] May 1, 1984

[54] DENTAL TREATMENT APPARATUS

[75] Inventor: Stefan Beier, Biberach, Fed. Rep. of Germany

[73] Assignee: Kaltenbach & Voight GmbH & Co., Fed. Rep. of Germany

[21] Appl. No.: 318,067

[22] Filed: Nov. 4, 1981

[30] Foreign Application Priority Data

Nov. 28, 1980 [DE] Fed. Rep. of Germany ....... 3045011

[51] Int. Cl.$^3$ ..................... G09G 3/00; G06K 15/18
[52] U.S. Cl. ................................. 340/706; 340/802;
340/825.37; 433/28; 433/101
[58] Field of Search ........... 340/706, 715, 802, 825.37;
433/28, 101

[56] References Cited

U.S. PATENT DOCUMENTS 463,001 11/1891 Smith ................................. 340/715
4,180,812 12/1979 Kaltenbach et al. ............... 340/706

Primary Examiner—Marshall M. Curtis
Attorney, Agent, or Firm—Scully, Scott, Murphy & Presser

[57] ABSTRACT

A dental treatment apparatus having a plurality of dental instruments which are adapted to be deposited and releasably retained in an instrument holding device. The dentist is a position to store for the individual treatment instruments operating data of his own selection which will constitute fixed values. The treatment instrument will begin with these fixed values when taken into operation. However, the dentist can deviate from the fixed values and vary the operating data. The fixed values, as well as the varied operating data can be read off by the dentist on a display arrangement. After termination of the treatment, the treating instrument upon again being placed in operation commences at the stored fixed value. A data converter provides that the operating data are indicated on the display arrangement. It is possible to call up, by means of a single selecting sequence, the sets of data informations typical for treatments by all instruments which are to be employed.

8 Claims, 4 Drawing Figures

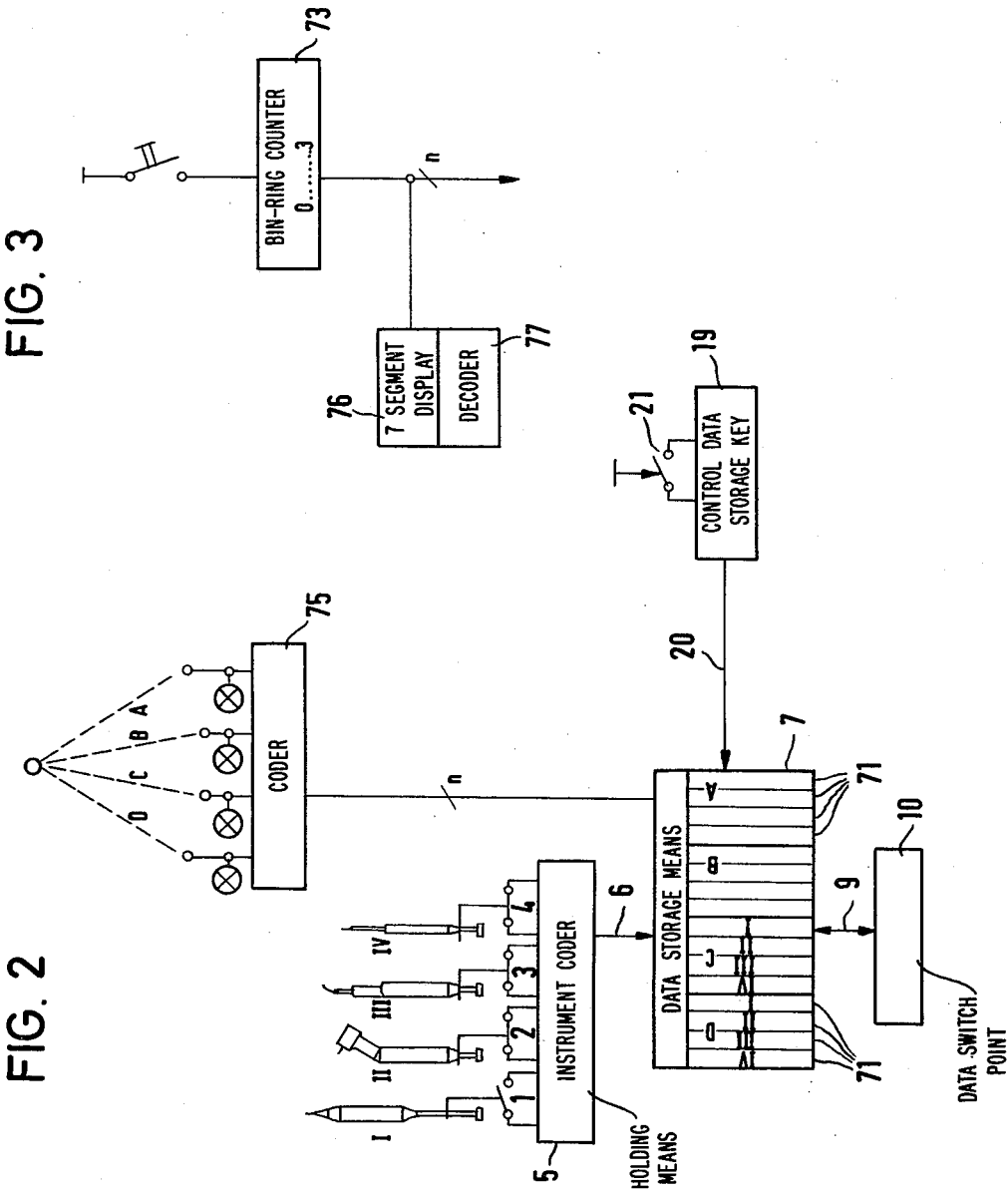

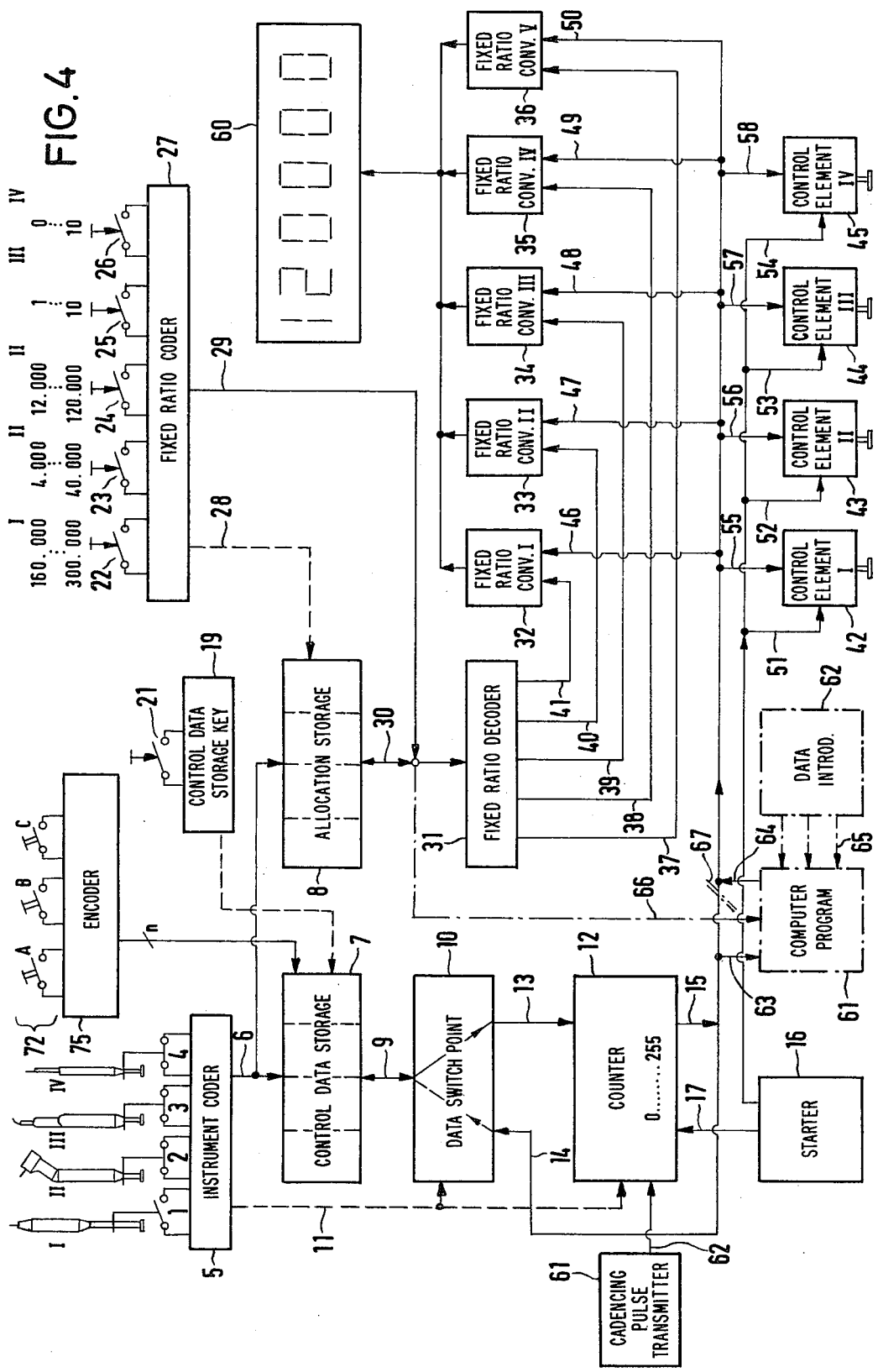

DENTAL TREATMENT APPARATUS

BACKGROUND OF THE INVENTION

1. Field of the Invention

The present invention relates to a dental treatment apparatus having a plurality of dental instruments which are adapted to be deposited and releasably retained in an instrument holding device.

2. Discussion of the Prior Art

A dental treatment apparatus of this type is described in Kaltenbach et al. U.S. Pat. No. 4,180,812, assigned to the common assignee of the present application, by means of which the dentist is a position to store for the individual treatment instruments operating data of his own selection which will constitute fixed values. The treatment instrument will begin with these fixed values when taken into operation. However, the dentist can deviate from the fixed values and vary the operating data. The fixed values, as well as the varied operating data can be read off by the dentist on a display arrangement. After termination of the treatment, the treating instrument upon again being placed in operation commences at the stored fixed value. A data converter provides that the operating data is indicated on the display arrangement.

In the treatment apparatus described in U.S. Pat. No. 4,180,812 there is further provided that upon the withdrawal of a treating instrument from its depository in the holding device a switch which is associated therewith is actuated. These switches are connected with an instrument-encoder which generates an address signal characteristic of the currently withdrawn instrument. The control data-storage in the treatment apparatus pursuant to U.S. Pat. No. 4,180,812 evidences a number of registers corresponding to the number of treatment instruments, wherein each register is associated with one treatment instrument. The control data-storage has the address signal which is triggered by the actuating switches conducted thereto in order to activate the register which is associated with the instrument withdrawn from its depository, for the connection with the data switch-point.

Through the dental treatment apparatus which is known from U.S. Pat. No. 4,180,812, for each instrument there can be called up individually the control data. Upon an exchange of the current treatment instrument, the treating personnel must select a new set of data for the then employed instrument.

During a typical dental treatment, the dentist will not only utilize one instrument but, in most instances, a plurality of instruments. Therefore, it is desirable that in conformance with the contemplated type of treatment the control data for all instruments which are to be employed can be concurrently selected, so that upon an instrument exchange the treating personnel need not again require to individually call up the desired set of data for each treatment instrument.

SUMMARY OF THE INVENTION

Accordingly, it is an object of the present invention to provide a dental treatment apparatus wherein it is possible for predetermined, typical treatment methods to call up, by means of a single selecting sequence, the sets of data informations typical for treatments by all instruments which are to be employed.

The invention increases the particular portion of the treatment process which the dentist can effectuate without correction by means of stored operating data. As control data information within the context of the invention there is designated the totality of the control data values which are associated with the individual treating apparatuses. By "control data word", in contrast therewith, there is meant the currently selected operating parameter of an individual treating instrument.

By means of the selecting arrangement there can be made a selection between different sets of control data. The (actual) set of control data which is currently in use is indicated through a suitable display arrangement.

The programming of the storage which is described in U.S. Pat. No. 4,180,812 is presently effected only within the actuated (actual) set of control data for each instrument. Thus, there is selected the set of control data by means of the control data set-preselection switch. Within the selected set of control data each depository arrangement has thus associated therewith a control data word (in effect, the individual instrument-related data).

Inasmuch as there is made available to the treating personnel a plurality of sets of control data there is saved the constant new setting of predetermined control data, for example, the rotational speed, the spray condition, the direction of rotation and so forth. The work is rendered easier and time is saved.

Since in many individual instances the sequence of the treatment and the individual utilization of a treating instrument is not predictable and, accordingly, cannot be preprogrammed. It is intended that one of the selectable sets of control data be so preprogrammed that from the very beginning all instruments evidence a median rotational speed or operating intensity, so that thereby proceeding from these median values the current necessity for change of the control data can be restricted to a minimum.

BRIEF DESCRIPTION OF THE DRAWINGS

Reference may now be had to the following detailed description of an exemplary embodiment of the invention, taken in conjunction with the accompanying drawings; in which:

FIG. 2 illustrates a schematic representation for the selection of sets of control data;

FIG. 3 shows an alternative embodiment of the arrangement illustrated in FIG. 2; and FIG. 4 is a schematic block circuit diagram showing the selecting arrangement for the sets of control data ancillary to the above-mentioned U.S. patent.

DETAILED DESCRIPTION

Figure 1:
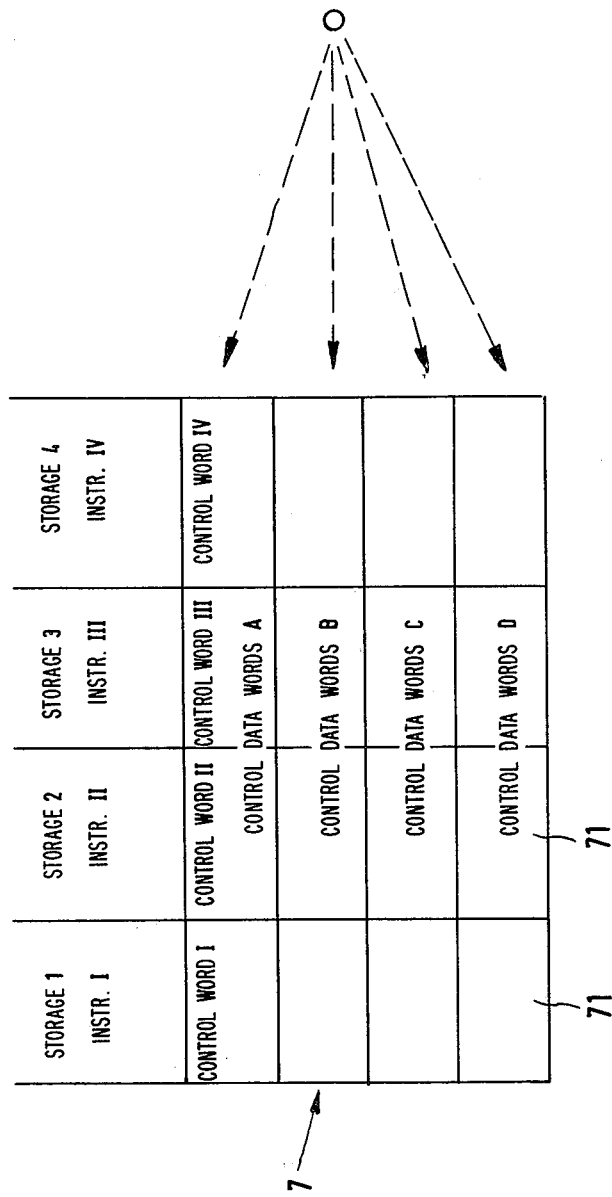
FIG. 1 illustrates a schematic representation for the selection of sets of control data A-D with individual control words associated with the individual instruments.

The specification of U.S. Pat. No. 4,180,812, which issued to Kaltenbach et al. on Dec. 25, 1979 is hereby incorporated herein by reference thereto.

Illustrated in FIG. 1 is the schematic of the selection arrangement by means of which there can be obtained the inventive dental treatment apparatus. The individual instruments I-IV, which are located on corresponding depositories or holders 1-4, have individual control words stored in the control data storage 7 in corresponding registers 71, which currently have as the content a predetermined operating condition of one of the instruments I-IV. An entirety of currently four such control words, of which each one is associated with respectively one of the instruments I-IV, forms a set of control data. In FIG. 1 there is illustrated that it is possible to have a selection between four different sets of control data A through D. The number of the registers necessary in the storage, in the illustrated exemplary case, consists of 4×4=16, since four instruments are present in the treating apparatus and in a selection capability should be available between four different sets of control data.

FIG. 2 schematically illustrates the manner in which, with the aid of a preselection switch, there can be selected the desired set of control data. Through the preselection switch there is selected a predetermined input of a coder 75 which conducts thereto a predetermined output signal to the addressing decoder of the control data storage. In accordance with the measure of this signal are there selected the corresponding registers and conducted further through the data switch-point.

In FIG. 2 there is further illustrated that through the intermediary of the inventive arrangement, a program can also be carried out. Present for this purpose is a control data storage key 19 upon the actuation of which a pulse transmitter 19 is caused to transmit through a conductor a setting impulse to the control data storage 7. The recalculated operating data of the currently employed instruments are then stored in the registers.

Illustrated in FIG. 3 is an alternative embodiment for the selection of the sets of control data. In this embodiment there is provided a BIN-ring counter 73 which is connected with a seven-segment display 76. This in turn has connected ahead thereof a further joint decoder and driver 77.

FIG. 4 illustrates a schematic circuit block diagram for the inventive dental treatment apparatus. It essentially corresponds to the schematic circuit block diagram illustrated in U.S. Pat. No. 4,180,812 the disclosure of which is incorporated herein by reference. The control data storage is acted upon by an additional address conductor which is located at the output of the preselection switch and coder 75. Connected to this coder 75 is a preselection switch 72 through which there can be selected predetermined inputs of the coder 75. The preselection switch, for example, can be a rotary switch or also a pressure-key switch.

What is claimed is:

1. A dental treatment apparatus having a plurality of dental instruments, a control for each instrument, and a display means for displaying the magnitude of the operating parameter of the instrument, said treatment apparatus comprising:
   (a) a data storage means having a plurality of registers for storing a plurality of predetermined control data words for each of said instruments,
   (b) a preselection switch means for selecting one of said control data words for said instrument as it is initially withdrawn from said holding means, said preselection switch means also being operable to selectively retrieve a control data word for each of said instruments from a plurality of data words previously entered for each instrument,
   (c) switch means operable to alter the selected control data word to a value different from said control data word value, and selectively store said value in said data storage means as a control data word,
   (d) a control means for driving each of said instruments in response to the control data word selected by said preselection means,
   (e) a display means to display the magnitude of the operating parameter derived from the control data word used to drive the dental instrument, said display means adapted to display variable values as said control data word is varied.

2. Dental treatment apparatus as claimed in claim 1, where said switch means for altering said sets of control data includes a BIN-ring counter and a foot-activated switch.

3. Dental treatment apparatus as claimed in claim 1, wherein said switch means for altering said sets of control data includes a BIN-ring counter and a manually-activated switch.

4. Dental treatment apparatus as claimed in claim 1, wherein said switch means for altering said sets of control data are located within a dental foot-operated actuator.

5. Dental treatment apparatus as claimed in claim 4, which further includes a control data storage key connected between said control means and said data storage means, and actuatable through a foot-operated switch means.

6. Dental treatment apparatus as claimed in claim 1, which further includes actuating switches actuated in response to withdrawal of a treating instrument; and an instrument encoder connected with said switches for generating an address signal characteristic of the treating instrument presently withdrawn from the holding means in the apparatus.

7. Dental treatment apparatus as claimed in claim 1, which further comprises a forward-backward counter in said control means; an actuator connected to said counter for resetting the latter, said counter being connected with the data storage means and said display means.

8. Dental treatment apparatus as claimed in claim 7, said counter having a pulse input connected with a synchronizing pulse transmitter, the setting input being connected to the data storage means through a branch of a data switch-point whereby the data switch-point and the counter are activated by a data set command for the counter.

* * * * *